United States Patent [19]

Crowe

[11] Patent Number: Plant 5,286

[45] Date of Patent: Sep. 25, 1984

[54] *SYZYGIUM PANICULATUM* (PEARLY SHOWERS)

[76] Inventor: Fred Crowe, 3758 Narragansett Ave., San Diego, Calif. 92107

[21] Appl. No.: 353,806

[22] Filed: Mar. 1, 1982

[51] Int. Cl.[3] ..... A01H 5/12

[52] U.S. Cl. ..... Plt./51

[58] Field of Search ..... Plt./51

*Primary Examiner*—Robert E. Bagwill

[57] ABSTRACT

A new and distinct variety of *Syzygium paniculatum,* which is a periclinal chimera arising from the stump of a normal *Syzygium paniculatum* is presented. This new variety possesses attractively variegated leaves. Specifically, the mature leaves are a combination of medium and deep greens and have creamy white margins. The overall appearance of the mature plant is pearly when viewed from a distance. The new variety retains the upright form and drought tolerance of the parent. The leaves, prior to dropping change color ad show blushes of orange and gold. Flowers are rare and fruit even rarer, usually developing without any seed.

17 Drawing Figures

SPECIFICATIONS

The present invention relates to a new and distinct variety of *Syzygium paniculatum,* and is a periclinal chimera resulting from chemical manipulation resulting in the mutation.

The primary features of this new variety which connote its distinctive advance over existing types are foliage which is unusually variegated and bud to fruit development without flowering or fertilization by parthenocarpy. The foliage in this cultivar regularly consists of white-edged multi-toned green leaves which emerge plum colored and fade through various rose hues before finally developing their mature coloration. Prior to dropping older leaves, the color changes again. This time it shows apricot and peach colors. The following color terminology is in accordance with the Robert F. Wilson, Royal Horticultural Society Color Chart (2 volumes, 1938–1941), London, England.

Flowers rarely develop. Instead buds emerge, fatten and develop without ever opening, into fewer and smaller than normal sized fruit without seed. (FIG. 1) This new variety has been named the Pearly Showers variety.

EXPLANATION OF PHOTOGRAPHS

A. Overall appearance of the shrub including some of the pure creamy white, red stemmed attendant foliage.

B. Close-up view of emerging burgundy toned leaves. Note the half white-tipped leaf.

C. Extreme close-up view of emerging leaves showing deep red where green will later show.

D. Pale rose hued area of note which will later be pure white.

E. Leaf showing axial demarkation between variegation and white.

F. View of an axial divided leaf with normal green and white characters.

G. Emergent pure white foliage.

H. Early flower bud development. At this stage flower buds appear normal.

I. Flower buds beginning to swell.

J. Sepals starting to fuse and show color without the flower opening. Note that many buds have dropped from this terminal cluster.

K. Swollen buds, fused sepals and normal color development of fruit. Note the older leaves are beginning to turn peach color at the margins. Note that the parts of the leaves with chlorophyll have continued to outgrow the white areas resulting in a curled and lumpy leaf.

L. End view of parthenocarpic fruit. At this point, the fruit is easily dislodged from the branch end. It never fully develops normal deep purple color or normal size. Close inspection of the fruit reveals the petals, stamens and pistil tightly enclosed within the fused sepals beneath the swollen ovary wall. No seed is present in such fruits.

M. View of cutting with emergent roots.

N. View of one year old potted cutting.

The following is a detail description of the new variety.

Plant: Small vigorous single or multi-trunked tree with a dense foliage crown. Ultimate height unknown but presently about 15 feet tall and seven feet wide. It is probable that in cultivation this cultivar will reach the minimum height of 30 feet normally achieved by *Syzygium paniculatum.* It has already exceeded the recorded height for *Syzygium paniculatum* 'Variegatum' as published in *Pacific Horticulture,* Winter 1979–1980. Considering the vigor of this new cultivar, it is possible that it will ultimately achieve 30 to 60 feet in height which is closer to the normal height for the species. Exceptionally drought tolerant.

Leaves: Simple shiny, ovate to lance shaped, narrowed toward each end, somewhat acuminate at the apex, 1½" to 2" long, short petioled, arranged in opposite pairs with entire margins. Leaves are carried on somewhat pendent branchlets. New leaves emerge in April or May, normal for the species. Color is single toned Amber Yellow 505/1,2,3, and Egyptian Buff 407/2,3 at the edges, variable tones of color ranging from Willow Green 00862/1,2,3 to Spinach Green 0960/1 in the center. Newest growth is China Rose 024/3, Spinel Red 0023/2 or Dawn Pink 523/2 with Garnet Brown 00918, Oxblood Red 00823 or China Rose 02411 color where green parts will eventually be. Occasionally leaves are pure white or divided between white and variegated, green and variegated or white and green along the leaf axis. Rarely normal Spinach Green 0960/1. As leaves age, the chlorophyll producing areas grow faster than the white edges resulting in a decidedly lumpy or sculptured texture, a feature which is unique to this cultivar. Prior to shedding older leaves, Straw Yellow 604/3 to Orpiment Orange 10/3 or Spanish Orange 010/2 color develops, especially in the areas that were formerly white. This color change differs markedly from the reported leaf coloration in *Syzygium paniculatum* "Variegatum".

Flowers and fruit: Normal flowers rarely appear. When they do appear, it is during Spring, the normal time of flowering for the species. They are white or whitish, ½" to 1" across with numerous, conspicuous stamens. They appear in small clusters, terminal and on the ends of short branchlets or long peduncles and therefore showing beyond the foliage when present. (FIG. 2) Though flowers rarely develop, buds emerge and instead of opening normally, they continue to swell. The sepals fuse, except at the very tip and a miniature fruit develops parthenocarpicly, approximately at the normal fruiting time for the species. When this phenomenon occurs, most buds are dropped before significant size is attained. Those buds which eventually achieve fruit formation produce a berry not only much smaller than normal but also much paler in color, Magenta 27/1,2,3 or Phlox Pink 625/3 (FIG. 1). Parthenocarpic fruit development as observed in this plant has ornamental horticultural advantages. First, because the plant often fails to flower, bees are not attracted to it. Second, because of the limited, small sized, lightly colored, seedless fruit production, the normal messy staining berry drop and attendant unwanted seed germination is avoided. The parthenocarpic fruit lacks a seed, however the berry does contain residual petals, stamens and pistil. The swollen ovary wall and sepals form the majority of the fruit. This unusual form of parthenocarpy differs from the usually observed in other unrelated plants in-so-far as no flower ever appears. Parthenocarpic fruit development is not reported for *Syzygium paniculatum* 'Variegatum' at all. Asexual reproduction is probably the only method of propagation as those berries which did develop from the rare flowers, failed to remain attached to the plant until mature.

BACKGROUND OF VARIETY DEVELOPMENT

In 1976 I decided to remove an extremely tall, normal *Syzygium paniculatum* which grew outside our back door. Because the plant grew very close to a rock wall, I was unable to remove the stump. This drought tolerant shrub tends to secure itself with very deep roots which are very difficult to remove. I cut the stump level about four feet above the soil level and placed a copper sun dial on top of it. The stump responded to my severe butchering by sprouting from the base above the soil level with abundant normal, vigorous foliage.

Repeated attempts to discourage the sprouting stump met with failure. Chopping and cutting it off did not succeed for long.

My wife and I started dumping various chemicals on the sprouting stump. Such ordinary chemicals as laundry bleach and doggie dip were disposed of on the stump for several months with some success. Late in 1976, when the stump failed to sprout after a rather long period, we decided that our efforts had succeeded. In early 1977, however, the stump sprouted anew, this time with pure white foliage and no normal colored leaves. It looked attractive but I felt certain that the lack of chlorophyll would eventually cause the white foliage to fail. When it began to wither we celebrated our final triumph over the sprouting stump. Almost as soon as the pure white foliage totally withered and died, a new sprout emerged. The new growth showed only the variegated foliage and seemed quite vigorous.

At this point, I recognized the potential ornamental horticultural value of the developing shrub and ceased trying to kill the stump. I began to encourage the varied growth instead.

In early 1978 I felt the plant had developed sufficient biomass to allow the removal of a few cuttings. These I tried to root. Vermiculite was used as a rooting substrate, and the cuttings were dipped first in water to wet the cut ends, then into a commercially available rooting hormone. None developed roots, however. Throughout 1978 and 1979 I continued to try to root cuttings and in winter of 1979 the first hope of success seemed at hand. I had realized that cuttings taken in winter (November through January) just prior to the initiation of new growth on the cultivar, were most likely not to wilt. This season appears to be the optimum for successful rooting. Spring of 1980 brought confirmation of what had seemed a success. I had indeed rooted cuttings. Since that time my rate of success has improved as I mastered the technique of season and method of successful rooting of scions. Included in the photo series is a picture of one of the rooted cuttings, and of a year old established cutting in a gallon plastic can. All vegetatively produced cuttings share identical foliar characteristics with the original plant and one of the rooted cuttings actually produced the unusual parthenocarpic fruit as well, unusual for such a small plant.

I claim:

1. A new and distinct variety of *Syzygium paniculatum*, characterized as a novelty by its unusual leaf color variegation, its parthenocarpic fruit development and vigorous growth habit substantially as shown and described.

* * * * *

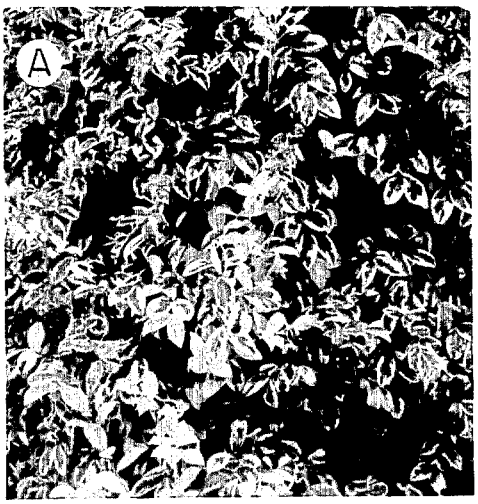
A
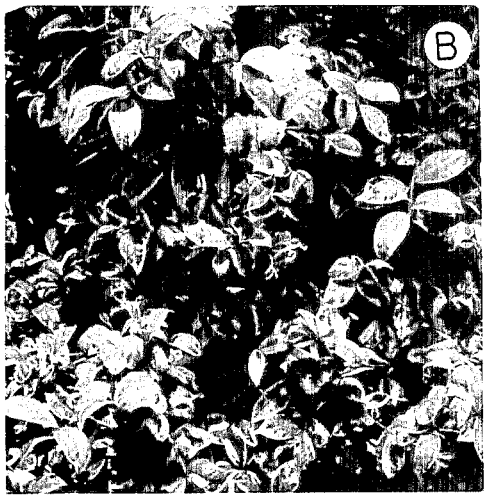
B
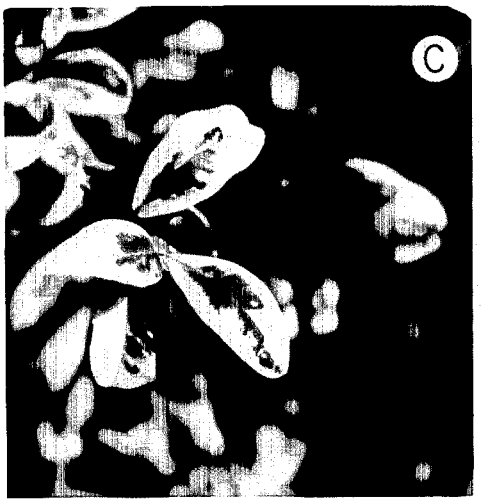
C
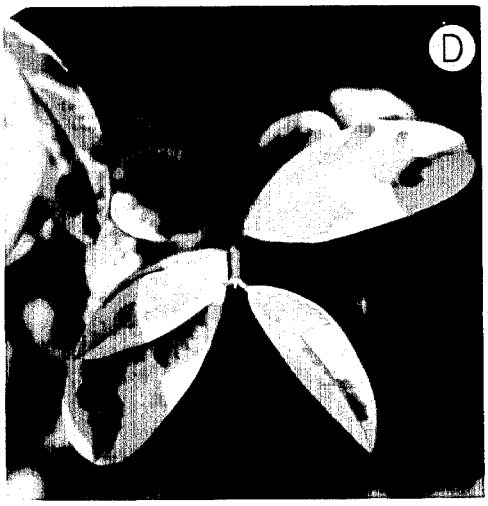
D
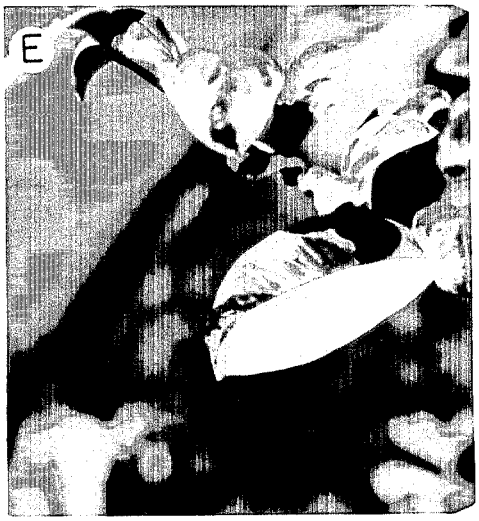
E
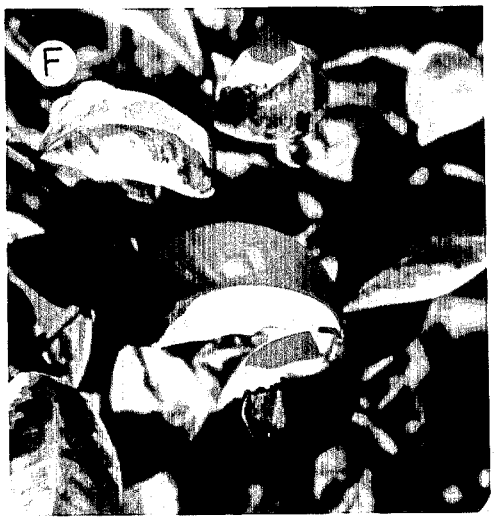
F

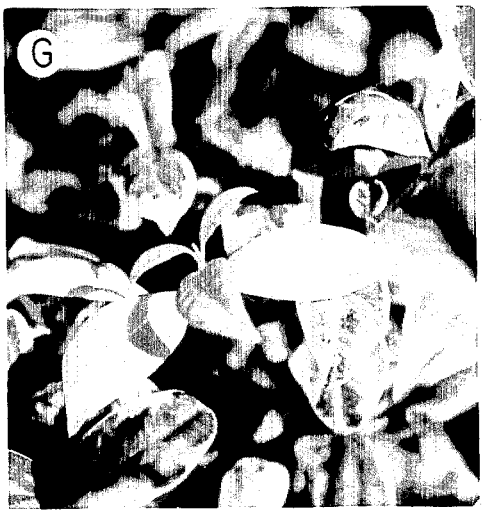
G
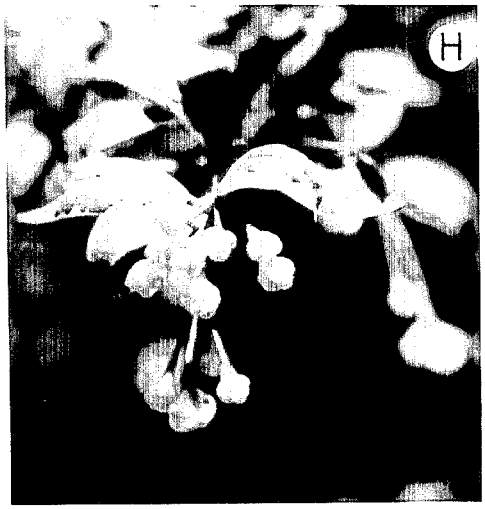
H
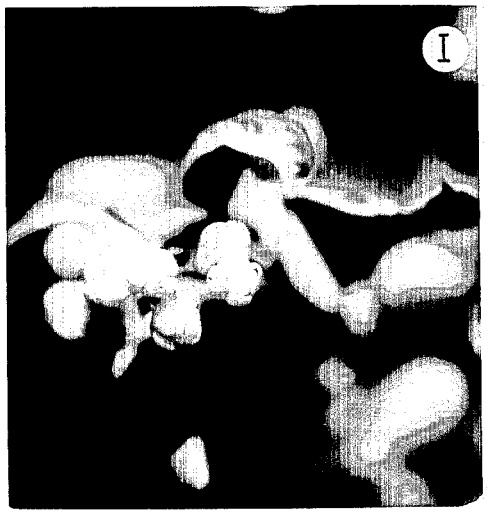
I
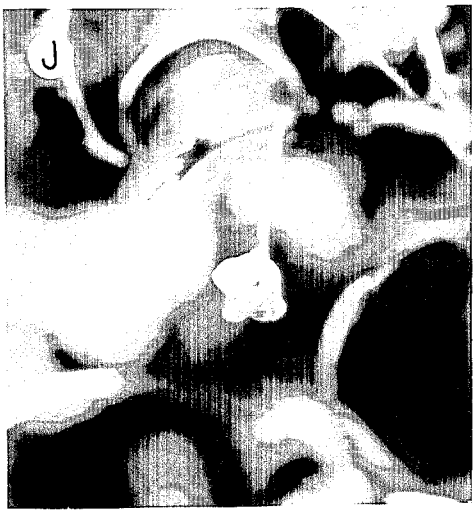
J
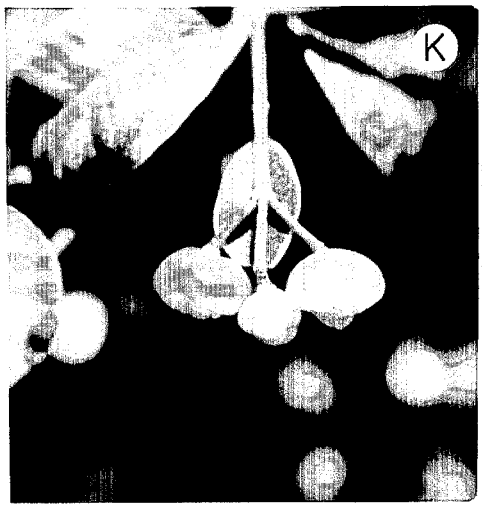
K
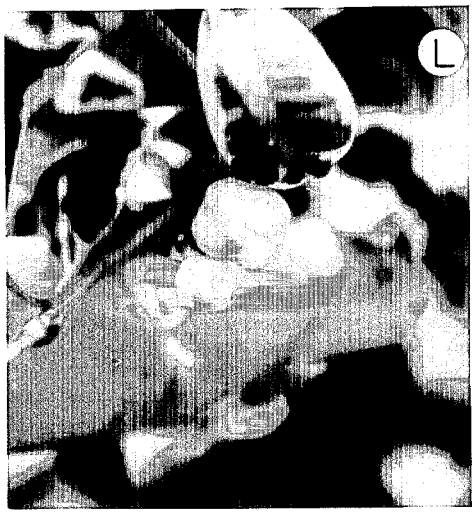
L

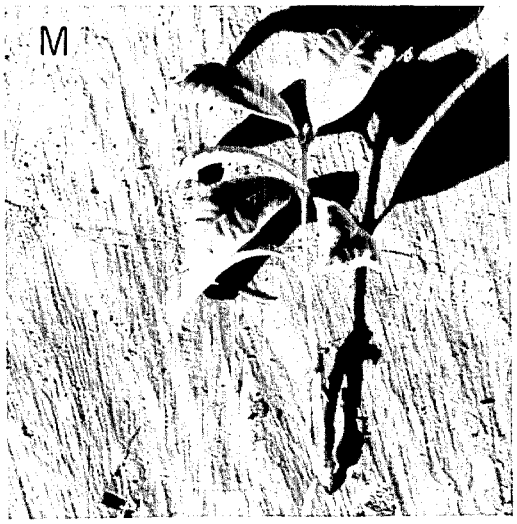
M
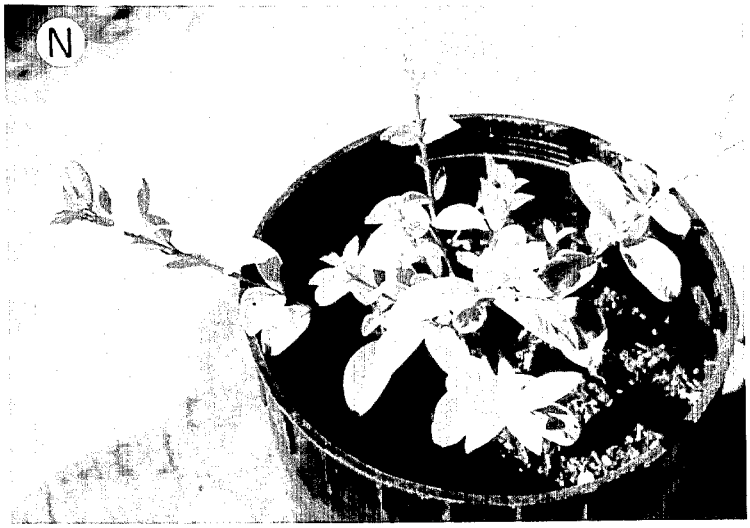
N

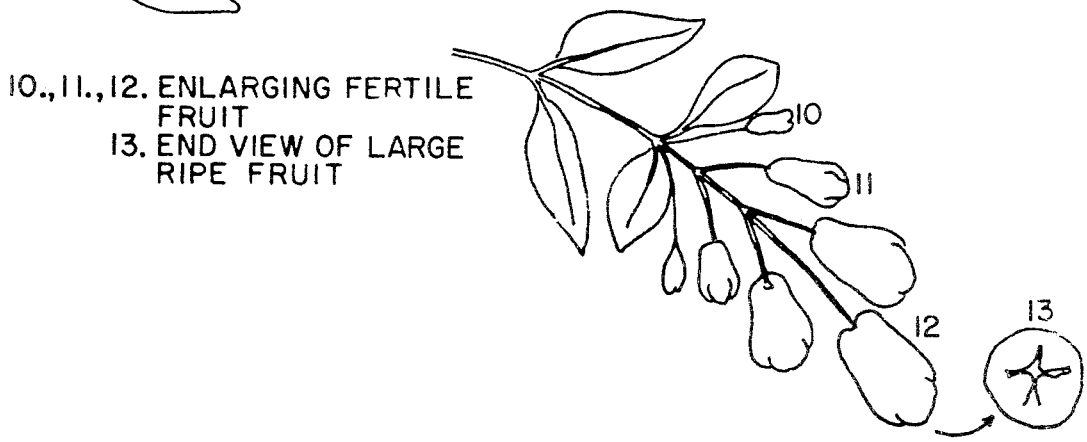

PARTHENOCARPIC FRUIT DEVELOPMENT (FIG. 1)
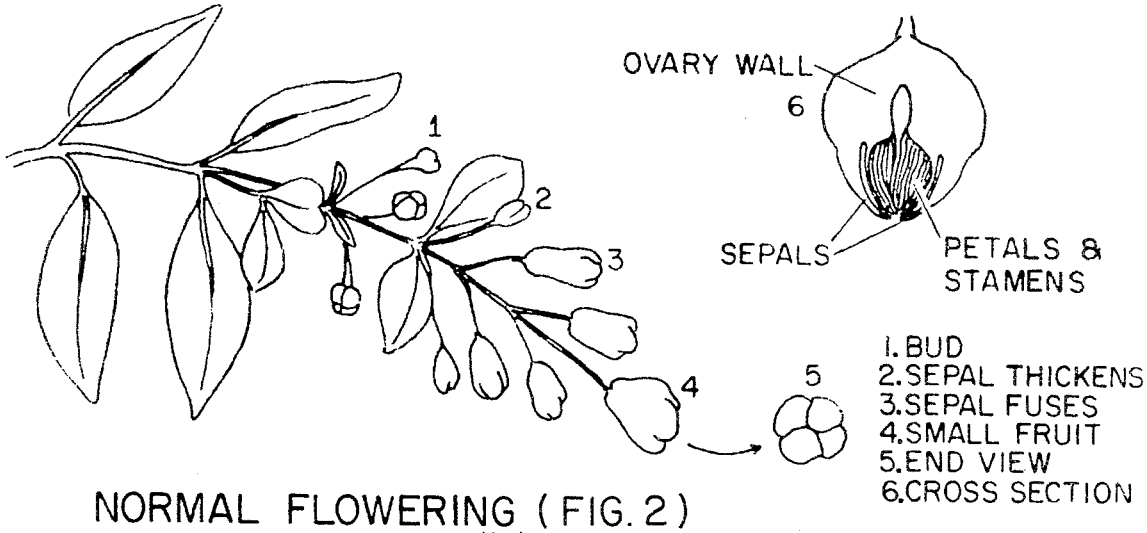
NORMAL FLOWERING (FIG. 2)
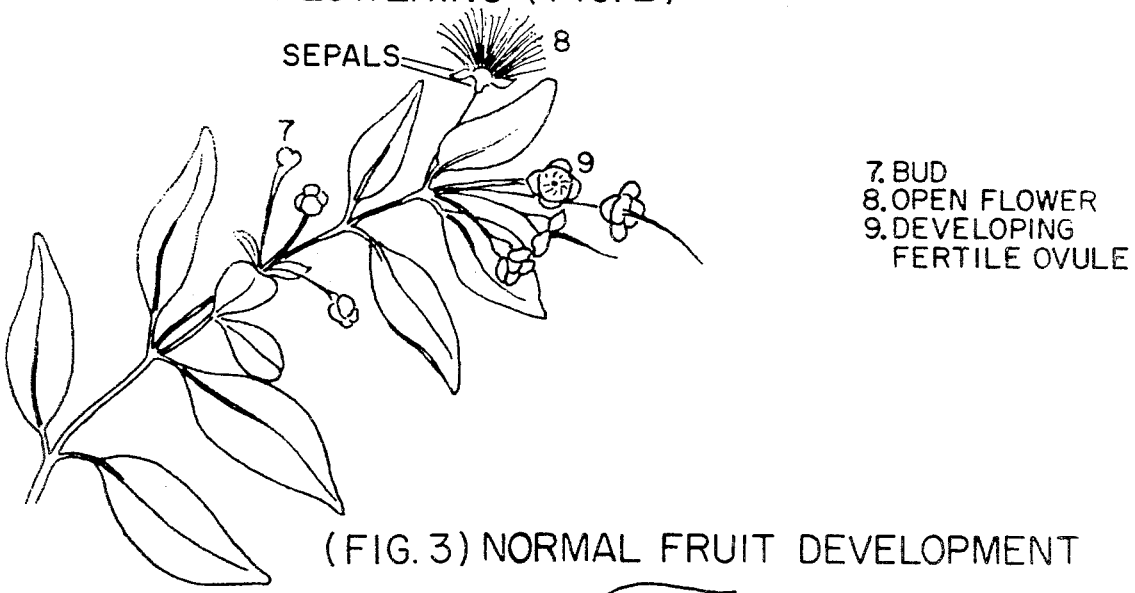
(FIG. 3) NORMAL FRUIT DEVELOPMENT